US00PP26324P3

(12) United States Plant Patent
Suphachadiwong

(10) Patent No.: US PP26,324 P3
(45) Date of Patent: Jan. 19, 2016

(54) *DENDROBIUM* ORCHID PLANT NAMED 'SPCDW1007'

(50) Latin Name: ***Dendrobium* hybrid**
Varietal Denomination: SPCDW1007

(71) Applicant: Thumrong Suphachadiwong, Chonburi (TH)

(72) Inventor: Thumrong Suphachadiwong, Chonburi (TH)

(73) Assignee: Suphachatawong Innovation (TH)

( * ) Notice: Subject to any disclaimer, the term of this patent is extended or adjusted under 35 U.S.C. 154(b) by 173 days.

(21) Appl. No.: 13/987,938

(22) Filed: Sep. 16, 2013

(65) Prior Publication Data

US 2014/0082798 P1 Mar. 20, 2014

(30) Foreign Application Priority Data

Sep. 17, 2012 (QZ) ..... PBR 2012/1961

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — June Hwu
(74) *Attorney, Agent, or Firm* — Cassandra Bright

(57) ABSTRACT

A new and distinct *Dendrobium* cultivar named 'SPCDW1007' is disclosed, characterized by a large purple flower color and good disease resistance. The new variety is a *Dendrobium*, typically produced as an indoor ornamental plant.

1 Drawing Sheet

Latin name of the genus and species: *Dendrobium* hybrid.
Variety denomination: 'SPCDW1007'.

BACKGROUND OF THE INVENTION

This application relates to a new cultivar of *Dendrobium* hybrid. The new variety is the product of a planned breeding program. The new variety originated as a seedling from the crossing of the unpatented, proprietary seed parent *Dendrobium* '125T' with the unpatented, proprietary pollen parent referred to as *Dendrobium* 'WS'. The crossing was made by the inventor in his research greenhouse in Chonburi, Thailand in December of 2001.

The new variety was first selected by the inventor, Thumrong Suphachadiwong, a citizen of Thailand, in a research greenhouse belonging to the inventor in Chonburi, Thailand. After identifying the new variety as a potentially interesting selection, the inventor continued confidential testing and propagation of 'SPCDW1007', assessing stability of the unique characteristics of this variety.

Asexual reproduction of the new cultivar 'SPCDW1007' was first performed at a commercial laboratory belonging to the inventor in Chonburi, Thailand by tissue culture propagation was performed using meristem culture in March of 2006. The very growing centre of a new growth bud is taken and grown on by agitating constantly in a special nutrient rich liquid until the cell mass is large enough to be split in to small sections these are then either grown on in to plants or the process is repeated to produce more tissue for growing on. This method is often used to mass produce a specific hybrid for commercial purposes. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SPCDW1007' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1007.' These characteristics in combination distinguish 'SPCDW1007' as a new and distinct *Dendrobium* cultivar:

1. Dark purple flowers.
2. Large flower size.

PARENT COMPARISON

Plants of the new cultivar 'SPCDW1007' are similar to the seed parent, *Dendrobium* '125T' in most horticultural characteristics. However the new variety, 'SPCDW1007' differs from '125T' in the following characteristics:

1. Larger flowers.
2. Different flower color.
3. Good disease resistance.

Plants of the new cultivar 'SPCDW1007' are similar to the pollen parent, *Dendrobium* 'WS' in most horticultural characteristics. However the new variety, 'SPCDW1007' differs from 'WS' in the following characteristics:

1. Purple flower color, parent flower color is white.
2. Smaller plant size.
3. Smaller flower size.

COMMERCIAL COMPARISON

'SPCDW1007' is similar in most horticultural characteristics to the unpatented commercial variety *Dendrobium* 'TROP0012' in most horticultural characteristics. However the new variety, 'SPCDW1007' differs from 'TROP0012' in the following characteristics:

1. Darker purple flower color.
2. Darker green leaves.
3. Longer narrower lip.
4. Different sepal shape

BRIEF DESCRIPTION OF THE PHOTOGRAPH

The accompanying photograph in FIG. 1 illustrates in full color a typical plant of 'SPCDW1007' grown in a commercial greenhouse in Honselersdijk, the Netherlands. The plant is approximately 3 years old from a plantlet, in a 10.5 cm pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SPCDW1007' plants grown in a commercial greenhouse in Honselersdijk, the Netherlands. The plant is approximately 3 years old from a plantlet, in a 10.5 cm pot. Temperatures ranged between 26° C. and 30° C. day and night. No photoperiodic or chemical treatments were given to the plants. The light sum was set at 5 moles per day and the plant was given shading and artificial light in order to come to the light sum of 5 moles per day. Both shading and artificial lightning were frequently applied in order to achieve the ideal light sum of 5 moles per day. Measurements and numerical values represent averages of typical plant types.

Botanical classification: *Dendrobium* hybrid 'SPCDW1007'.

PROPAGATION

Type of propagation typically used: Tissue culture propagation was performed using meristem culture. The very growing centre of a new growth bud is taken and grown on by agitating constantly in a special nutrient rich liquid until the cell mass is large enough to be split in to small sections these are then either grown on in to plants or the process is repeated to produce more tissue for growing on. This method is often used to mass produce a specific hybrid for commercial purposes.

Time to initiate roots: Tissue culture takes 18 months. After deflasking it takes another 9 to 12 months to get a well-rooted plant under average temperatures ranging between 26 en 30 degrees Celsius. After planting in the final pot, the young plant already has roots and those roots continue to grow in the end pot almost right away and certainly within 8 days.

Time to produce a rooted cutting/liner: Tissue culture takes 18 months. After deflasking it takes another 9 to 12 months to get a well-rooted plant under average temperatures ranging between 26 and 30 degrees Celsius.

Root description:

*Root color.*—Yellow-white to greyed-yellow, in between near RHS 158A and 161D.
*Average diameter.*—Average: 0.2 cm.
*Average length.*—Lateral roots average: 4.2 cm.

PLANT

Growth habit: Sympodial, upright.
Height from top of soil line to top of foliage: 27.0 cm.
Height from top of soil line to top of flowers: 56.6 cm.
Plant spread: 30.1 cm.
Normal pot size: 10.5 cm circular pot.
Growth rate: Moderate.
Number of leaves per plant: Average: 32.
Plant stem:

*Length.*—Approximately 12.4 cm.
*Diameter.*—Approximately 1.8 cm.
*Aspect.*—Approximately 75° angle to soil surface (=0°).
*Strength.*—Strong.
*Texture.*—Glabrous, very slightly glossy, axially ribbed.
*Color.*—Yellow-green, near RHS 147C and 147D, slightly striped axially, yellow-green; near RHS 144B, base greyed-green; near RHS 198D, axially striped grey-brown; 199D.

FOLIAGE

Leaf:

*Arrangement.*—Distichous.
*Average length.*—Approximately 11.0 cm.
*Average width.*—Approximately 4.7 cm.
*Shape of blade.*—Ovate to narrow ovate.
*Aspect.*—Leaves in an average angle of 75° to main stem (=0°).
*Apex.*—Acute.
*Base.*—Sheathing. Sheath length: Average 2.8 cm. Sheath width: Average 1.7 cm. Sheath color: Yellow-green, near RHS 147C and 147D, slightly striped axially, yellow-green; near RHS 144B.
*Margin.*—Entire.
*Texture of top surface.*—Glabrous, moderately glossy.
*Texture of bottom surface.*—Glabrous, very slightly glossy.
*Durability to physical stress.*—High.
*Color.*—Young foliage upper side: Green; near RHS 143A. Young foliage under side: Green to yellow-green; in between near RHS 143C and 144A. Mature foliage upper side: Green; near RHS 143A but darker. Mature foliage under side: Green to yellow-green; in between near RHS 143C and 144A, closest to 144A.
*Venation.*—Type: Parallel. Venation coloration: Upper Surface: Green; near RHS 143A but darker. Lower Surface: Green; near RHS 143B.
*Petiole.*—No petioles present.

FLOWERING CHARACTERISTICS

Flower bud:

*Rate of opening.*—Approximately 30 days from first emergence.
*Length.*—Approximately 2.8 cm.
*Diameter.*—Approximately 1.0 cm.
*Shape.*—Ovate, curved.
*Color.*—Purple; near N77B, base red-purple; near RHS 72A.

Peduncle:

*Length.*—Approximately 34.5 cm.

*Diameter.*—Approximately 0.25 cm.

*Aspect.*—Approximately 0° angle to stem.

*Strength.*—Strong.

*Texture.*—Glabrous, very slightly glossy.

*Color.*—Yellow-green; near RHS 144B.

Inflorescence:

*Flowers per stem.*—Average: 19.

*Inflorescence arrangement.*—Simple raceme.

*Inflorescence height.*—Approximately 28.0 cm (from lowest pedicel to top of inflorescence).

*Inflorescence width.*—Approximately 11.5 cm.

Individual flowers:

*Flower type.*—Single, orchidaceous (zygomorphic), typical for *Dendrobium.*

*Rate of opening.*—After the first flower has opened, it takes approximately four weeks before the top flower opens.

*Shape.*—Orchidaceous (zygomorphic), typical for *Dendrobium*, with three sepals, two lateral petals and a labellum (third petal).

*Height.*—Approximately 6.6 cm.

*Diameter.*—Approximately 7.3 cm.

*Depth.*—Approximately 3.2 cm.

*Fragrance.*—No fragrance.

*Persistent?.*—Non-persistent.

*Quantity of petals.*—Average: 3 (two lateral petals and a labellum (=third petal)) Only the two lateral petals are described here as such.

*Location of flowers.*—The individual flowers are positioned along the peduncle.

*Lip eye.*—Absent.

*Lip twisting.*—Absent.

*Lip undulation.*—Weak to Intermediate.

*Lip fringing of the margin.*—Absent.

*Lip pubescence.*—Absent.

*Callosities.*—Present on upper side at the base of the central lobe. Average length: 0.9 cm. Average width: 0.4 cm. Color: purple; in between near RHS N79B and N79C.

Petals:

*Arrangement.*—Oppositely placed on each side of the column.

*Length.*—Approximately 4.1 cm.

*Width.*—Approximately 3.1 cm.

*Shape.*—Broad obovate, slightly curved.

*Apex.*—Rounded.

*Base.*—Cuneate.

*Margin.*—Entire.

*Appearance.*—Both sides matte, velvety.

*Texture, upper forward surface.*—Glabrous, velvety.

*Texture, lower back surface.*—Glabrous, velvety.

*Color.*—When opening, forward surface: purple; near RHS N78A. When opening, back surface: Purple; near RHS N78B, with a lighter central band; near RHS N78C. Fully Opened, forward surface: Red-purple to purple; in between near RHS N74A and N78A, closest to N78A. Fully Opened, back surface: Purple; in between near RHS 77B and N78B, with a lighter central band; near RHS N78C and N78D. Fading, forward surface: not fading (colors same as Fully Opened). Fading, back surface: not fading (colors same as Fully Opened). Color Venation Fully Opened, forward surface: Venation indistinguishable from rest of surface. Color Venation Fully Opened, back surface: Venation indistinguishable from rest of surface.

Labellum:

*Lateral lobe.*—Shape: Ovate. Length: Average: 1.4 cm. Width: Average: 1.2 cm.

*Central lobe.*—Shape: Oblong. Length: Average: 2.1 cm. Width: Average: 1.3 cm.

*Shape.*—Deltoid, three-lobed, strongly involute.

*Length.*—Approximately 2.1 cm.

*Width.*—Approximately 1.7 cm (when "folded open", approximately 3.3 cm).

*Texture.*—Glabrous, velvety.

*Appearance.*—Matte, moderately velvety.

*Tip.*—Tips (apices) of the lateral lobes are obtuse. The central lobe of the labellum is obtuse, with a very small acute outer tip.

*Base.*—Attachment of the lateral lobes to the central lobe is broad cuneate. The location where the labellum is attached to the spur is characterized as having a broad cuneate base.

*Color.*—When opening, forward surface: Central lobe purple; in between near RHS N74A and N78A, closest to N78A, lateral lobes purple; near RHS N78A, base purple; in between RHS N74A and N78A but darker. When opening, back surface: purple; in between RHS 72B and 77B, with a white blotch at the base; near RHS NN155D (when not specified, the color designations of the labellum are for both the central lobe and the lateral lobes). Fully Opened, forward surface: Central lobe purple; in between RHS N74A and N78A, closest to N78A, lateral lobes purple; near RHS N78A, base purple; in between RHS N74A and N78A but darker. Fully Opened, back surface: Central lobe purple; near RHS N78B, lateral lobes purple; in between RHS 77B and N78B, with a white blotch at the base; near RHS NN155D. Fading, forward surface: Not fading. Fading, back surface: Not fading.

*Color venation fully opened, forward surface.*—Purple; near RHS N77C.

*Color venation fully opened, back surface.*—Venation indistinguishable from rest of surface.

*Margin.*—Entire.

*Callosites.*—Dimensions: Average: 1.1 cm long and 0.5 cm wide. Location: central placed on the labellum, colored purple; near RHS N79B and N78C.

Sepals:

*Quantity.*—Average: 3.

*Appearance.*—Matte, velvety.

*Length.*—Approximately 3.9 cm.

*Width.*—Dorsal sepal, approximately 1.7 cm. Lateral sepals, approximately 1.8 cm.

*Shape.*—Ovate to narrow ovate, slightly curved.

*Apex.*—Abruptly acute.

*Base.*—Broad cuneate.

*Margin.*—Entire.

*Texture.*—Glabrous, velvety.

*Sepal margin.*—Twisting: Absent. Undulation: Absent.

*Spur-like hood (mentum).*—Shape: Short triangular. Length: Short, average length: 0.7 cm. Width (horizontal): Average: 0.3 cm. Height (vertical): Average: 0.6 cm.

*Color.*—Forward surface: Purple; in between RHS N74A and N78A, closest to N78A, base and top purple to purple-violet; in between RHS N78C and N80B. Back surface: Purple; near RHS N78D, margins darker; N78C.

Pedicels:

*Length.*—Approximately 3.8 cm.

*Diameter.*—Approximately 0.2 cm.

*Angle.*—Approximately 60° angle to peduncle (=0°).

*Strength.*—Moderately strong.

*Texture.*—Glabrous, moderately glossy.

*Color.*—Purple; near RHS N78D, base yellow-green; 146C and 147B.

REPRODUCTIVE ORGANS

*Stamens, style and stigma fused into column?.*—Yes.

*Column length.*—Average: 0.5 cm.

*Column diameter.*—Average: 0.8 mm.

*Column color.*—Purple; near RHS 76C, margins darker; near N78A.

*Ovary.*—Position: Superior, placed directly above stigma. Diameter: Average: 0.15 cm. Color: Green-white; near RHS 157D.

*Stigma.*—Shape: Clavate. Color: White; near RHS NN155C and NN155D. Dimensions: Average: 0.1 cm high and 0.1 cm wide.

*Pollinia.*—Color: Yellow-orange; near RHS 14A. Dimensions: Average: 0.075 cm long and 0.1 cm wide. Quantity: 2.

OTHER CHARACTERISTICS

Disease resistance: Good resistance to normal disease of *Dendrobium.*

Drought tolerance and cold tolerance: Normal tolerance for *Dendrobium.*

Lastingness of flowers on plant: Lastingness of flowers when on the plant: Each individual flower can stay on the spike up to 9 weeks, counted from the day of opening of the flower until the day the flower drops. The actual lastingness of flowers depends of course, on several external circumstances.

Fruit/seed production: No fruits/seeds detected to date.

Pseudobulb:

*Longitudal section shape.*—Lanceolate to oblanceolate.

*Cross section shape.*—Circular.

What is claimed is:

1. A new and distinct cultivar of *Dendrobium* plant named 'SPCDW1007' as herein illustrated and described.

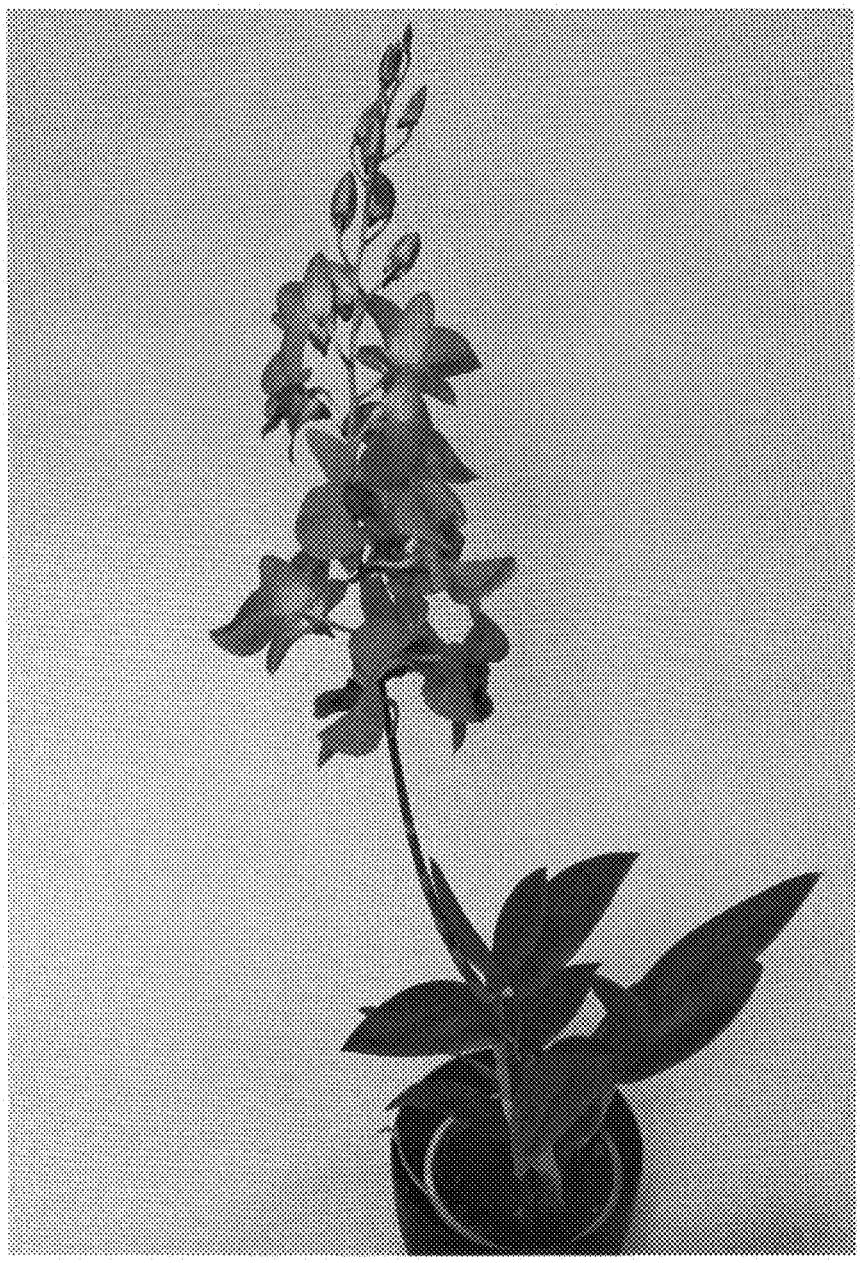

* * * * *